(12) United States Patent
Piepho et al.

(10) Patent No.: US 7,067,707 B2
(45) Date of Patent: Jun. 27, 2006

(54) PENTAFLUOROETHANE PRODUCTION METHOD

(75) Inventors: Eberhard Piepho, Hannover (DE); Vincent Wilmet, Wavre (BE); Olivier Buyle, Autre-Eglise (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 10/525,317

(22) PCT Filed: Aug. 22, 2003

(86) PCT No.: PCT/EP03/10083

§ 371 (c)(1), (2), (4) Date: Feb. 23, 2005

(87) PCT Pub. No.: WO2004/018394

PCT Pub. Date: Mar. 4, 2004

(65) Prior Publication Data

US 2006/0041174 A1    Feb. 23, 2006

(30) Foreign Application Priority Data

Aug. 23, 2002  (FR)  .................................. 02 10595

(51) Int. Cl.
*C07C 17/00* (2006.01)
(52) U.S. Cl. ........................ 570/175; 570/164; 570/165
(58) Field of Classification Search ................ 570/175, 570/164, 165
See application file for complete search history.

(56) References Cited

U.S. PATENT DOCUMENTS

| 5,728,884 A | 3/1998 | Hahn et al. |
| 5,847,245 A | 12/1998 | Franz et al. |
| 5,969,199 A | 10/1999 | Franz et al. |

FOREIGN PATENT DOCUMENTS

| DE | 44 45 529 | 3/1996 |
| EP | 0 634 383 | 1/1995 |

*Primary Examiner*—J. Parsa
(74) *Attorney, Agent, or Firm*—Connolly Bove Lodge & Hutz

(57) ABSTRACT

Process for the manufacture of pentafluoroethane, according to which tetrafluoroethylene is subjected to reaction with an organic nitrogenous base hydrofluoride at a temperature of greater than 100° C. and not exceeding 160° C.

19 Claims, No Drawings

PENTAFLUOROETHANE PRODUCTION METHOD

RELATED APPLICATIONS

This application is a national stage application (under 35 U.S.C. 371) of PCT/EP2003/010083 filed Aug. 22, 2003 which claims benefit to French application 02/10595 filed Aug. 23, 2002.

Pentafluoroethane (HFC-125) is a hydrofluoroalkane which is used, inter alia, in refrigerant compositions.

It is known to manufacture HFC-125 by hydrofluorination of chlorinated precursors, such as perchloroethylene or hydrochlorofluoroethanes. During such a manufacturing process, it is impossible to avoid the formation of chlorofluorocarbons (CFCs), in particular of CFC-115. CFCs are suspected of being involved in damage to the stratospheric ozone layer. Consequently, their content in HFC-125 has to be reduced on conclusion of the manufacturing process, which can prove to be complicated and expensive.

Patent Application EP-A-634383 discloses, inter alia, the manufacture of HFC-125 from tetrafluoroethylene in the presence of an organic nitrogenous base hydrofluoride. The productive output of HFC-125 is 40 mmol per hour and per litre of reaction medium.

It was desirable to make available a process for the manufacture of HFC-125 devoid of CFC-115 with an improved productive output.

The invention consequently relates to a process for the manufacture of pentafluoroethane, according to which tetrafluoroethylene is subjected to reaction with an organic nitrogenous base hydrofluoride at a temperature of greater than 100° C. and not exceeding 160° C.

In the process according to the invention, the temperature is often greater than or equal to 110° C. Preferably, the temperature is greater than or equal to 120° C. A temperature of greater than or equal to approximately 130° C. also gives good results. In the process according to the invention, the temperature is often less than or equal to 150° C. Preferably, the temperature is less than or equal to 145° C. A temperature of approximately 140° C. also gives particularly good results.

It has been found, surprisingly, that the process according to the invention makes it possible to manufacture HFC-125 devoid of CFC-115 starting from tetrafluoroethylene, under particularly effective conditions for productive output, without formation of by-products or decomposition of the organic nitrogenous base hydrofluoride. In particular, the process according to the invention makes it possible to increase the productive output of HFC-125 with respect to the teaching of the state of the art.

The productive output of HFC-125 by the process according to the invention is generally greater than or equal to 0.05 mol/h per litre of organic nitrogenous base hydrofluoride. It is often greater than 0.1 mol/h/l. More often, it is greater than or equal to 0.5 mol/h/l. The productive output of HFC-125 can even be greater than or equal to 1 mol/h/l.

In the process according to the invention, use is preferably made of a hydrofluoride of an organic nitrogenous base corresponding to the general formula (I):

[B·n HF]     (I)

in which B represents an organic nitrogenous base and n represents a whole or decimal number $\leq 4$.

Use may be made, as nitrogenous bases B corresponding to the formula (I), for example, of amines, including nitrogenous heterocycles. Specific examples of nitrogenous bases B correspond to the formula (II):

R1R2R3N     (II)

in which the R1, R2 and R3 residues can be identical or different and can signify:
a hydrogen atom,
an alkyl residue with 1 to 20, preferably 1 to 12, in particular 1 to 6, carbon atoms,
an alkenyl residue with 2 to 20, preferably 2 to 12, in particular 2 to 6, carbon atoms,
a cycloalkyl residue with 5 to 7 carbon atoms,
a cycloalkenyl residue with 5 to 7 carbon atoms,
an arylalkyl residue with 7 to 10 carbon atoms or
an aryl residue with 6 to 10 carbon atoms, which can also be substituted by $C_1$–$C_3$ alkyl or $C_1$–$C_3$ alkoxy groups.

The alkyl, cycloalkyl, arylalkyl and aryl residues mentioned are preferred in this case.

In addition, two of the R1 to R3 residues can form, together with the nitrogen atom which carries them, a 5- to 7-membered ring which can comprise an oxygen atom or an additional nitrogen atom. This ring consequently exhibits 5 to 7 members, one of which is the nitrogen atom and the others of which are preferably $CH_2$ groups. One of the $CH_2$ groups can also be replaced by an oxygen or nitrogen atom, this case, however, not being preferred.

The R1 to R3 residues can also form, together with the nitrogen atom which carries them, two or three 5- to 7-membered rings, preferably saturated rings, which can comprise additional nitrogen atoms, such as, for example, in hexamethylenetetramine or diazabicyclooctane.

In addition, the nitrogenous base B can be a 6-membered heterocyclic nucleus which can comprise one or two nitrogen atoms and which can also be benzo-fused, for example pyridine, pyrimidine or quinoline.

Organic nitrogenous bases B which are particularly preferred are tertiary amines, including N-heterocycles, with in all from 3 to 12 carbon atoms. Preferably, the tertiary amine is chosen from trimethylamine, triethylamine, tri(n-propyl)amine, isopropyldiethylamine, tri(n-butyl)amine, N,N-dimethylaniline, N-methylpiperidine, pyridine, quinoline, N,N,N',N'-tetramethylethylenediamine and hexamethylenetetramine. Tri(n-butyl)amine and triethylamine are particularly preferred. Triethylamine is even more particularly preferred.

The number n in the general formula (I) signifies the molar amount of HF per nitrogen atom of the base B and represents a whole or decimal number of less than or equal to 4. Preferably, n is a number of less than or equal to 3,5. More preferably, n is a number of less than or equal to 3. The number n generally represents a number of greater than or equal to 0.5. Preferably, n is a whole or decimal number of greater than or equal to 1, more particularly of greater than or equal to 1.5. More preferably, n is a number of greater than or equal to approximately 1.8. A number n of greater than or equal to 2 is more particularly preferred.

Specific examples of organic nitrogenous base hydrofluorides corresponding to the formula (I) which can be used in the process according to the present invention are indicated below:

$[(CH_3)_3N \cdot 2.5\ HF]$
$[(C_2H_5)_3N \cdot 2.0\ HF]$
$[(C_2H_5)_3N \cdot 2.5\ HF]$
$[(C_2H_5)_3N \cdot 3.0\ HF]$
$[(n\text{-}C_3H_7)_3N \cdot 3.0\ HF]$
$[(i\text{-}C_3H_7)_2(C_2H_5)N \cdot 2.6\ HF]$
$[(n\text{-}C_4H_9)_3N \cdot 2.0\ HF]$
$[(n\text{-}C_4H_9)_3N \cdot 2.5\ HF]$
$[(n\text{-}C_4H_9)_3N \cdot 3.0\ HF]$
$[(CH_3)_2N\text{—}CH_2\text{—}CH_2\text{—}N(CH_3)_2 \cdot 4.7\ HF]$
$[(CH_2)_6N_4 \cdot 2\ HF]$ In the process according to the invention, the use of [triethylamine.2.5HF], [triethylamine.2,0HF] or [tributylamine.2.0HF] is particularly preferred. [Triethylamine.2,5HF] and [triethylamine.2.0HF] are very particularly preferred.

The hydrofluorides corresponding to the formula (I) which can be used in the process according to the invention can be prepared by direct reaction of the amines with HF.

In the process according to the invention, the reaction between the tetrafluoroethylene and the organic nitrogenous base hydrofluoride is generally carried out at a pressure of greater than or equal to 2 bar. Preferably, the pressure is greater than or equal to 5 bar. A pressure of greater than or equal to 7 bar is more particularly preferred.

In the process according to the invention, the reaction between the tetrafluoroethylene and the organic nitrogenous base hydrofluoride is generally carried out at a pressure of less than or equal to 30 bar. Preferably, the pressure is less than or equal to 25 bar. A pressure of less than or equal to 20 bar is more particularly preferred.

The process according to the invention can be carried out, for example, in a bubble column, which can be composed of a corrosion-resistant metal, of borosilicate glass or of synthetic material, or in an autoclave made of an appropriate material. Preference is given to any apparatus resistant to the reactants and to the preferred pressures and to the preferred temperatures described above.

Generally, the addition of a solvent is not necessary. If the need arises, it is possible, however, also to operate in the presence of sufficient amounts of an aprotic solvent, such as dioxane, tetrahydrofuran, acetonitrile or N-methylpyrrolidone and N,N-dimethylformamide.

In this case, the amount of solvent generally does not exceed 80% by weight of the total weight of the reaction medium. The amount of solvent often does not exceed 60% by weight of the total weight of the reaction medium. When a solvent is employed, its amount is generally at least 20% by weight of the total weight of the reaction medium.

The process according to the invention can be carried out batchwise or continuously. Good results have been obtained continuously.

When the process according to the invention is carried out batchwise, the duration of the reaction is generally at least 10 minutes. The duration of the reaction is often at least 20 minutes. It is preferably at least 30 min. In this case, the duration of the reaction is generally at most 100 hours. The duration of the reaction is often at most 30 hours. It is preferably at most 5 hours.

When the process according to the invention is carried out continuously, the residence time, defined as the ratio of the volume of the reaction medium to the total gas flow rate at the inlet of the reactor, is generally greater than or equal to 5 min. The residence time is often greater than or equal to 10 min. The residence time is preferably greater than or equal to 20 min. The residence time is generally less than or equal to 10 h. The residence time is often less than or equal to 5 h. The residence time is preferably less than or equal to 3 h.

During the reaction, particularly when it is carried out continuously, it is possible to control the ratio of the organic nitrogenous base to the hydrogen fluoride in the organic nitrogenous base hydrofluoride. This control can be achieved, for example, by treatment of at least a fraction of the reaction medium with hydrogen fluoride, in particular by noncontinuous additions or by continuous addition of hydrogen fluoride to the reaction medium.

In an alternative form, it is possible to withdraw a fraction of the reaction medium comprising organic nitrogenous base hydrofluoride, to subject, outside the reactor, at least a portion of this fraction to treatment with hydrogen fluoride and then to recycle at least a portion of the treated fraction to the reaction medium.

When the ratio of the organic nitrogenous base to the hydrogen fluoride in the organic nitrogenous base hydrofluoride is controlled, the aim is generally to ensure that, overall, the number n in the organic nitrogenous base hydrofluoride in the reaction medium in the course of reaction does not reach a value below 70% of its initial value. This treatment is often carried out so that the number n does not reach a value below 80% of its initial value. Preferably, care is taken that the number n does not reach a value below 90% of its initial value.

If appropriate, care is generally taken that the number n in the organic nitrogenous base hydrofluoride in the reaction medium in the course of reaction does not exceed 150% of its initial value.

The HFC-125 can be isolated, for example, by distillation or by reduction in pressure and by condensation.

The HFC-125 obtained according to the process according to the invention is generally directly totally devoid of CFC-115.

The invention consequently also relates to a process for the manufacture of a refrigerant mixture devoid of CFC-115 (chloropentafluoroethane), according to which
(a) HFC-125 devoid of CFC-115 is manufactured according to the process according to the invention;
(b) the HFC-125 is mixed with at least one other hydrofluoroalkane chosen from HFC-32 (difluoromethane), HFC-134a (1,1,1,2-tetrafluoroethane) and HFC-143a (1,1,1-trifluoroethane).

In another aspect, the invention relates to a refrigerant composition devoid of CFC-115 comprising HFC-125 and at least one other hydrofluoroalkane chosen from HFC-32, HFC-134a and HFC-143a.

In yet another aspect, the invention relates to a process for the manufacture of a sterilizing gas mixture devoid of CFC-115, according to which
(a) HFC-125 devoid of CFC-115 is manufactured according to the process according to the invention;
(b) the HFC-125 is mixed with at least HFC-227ea (1,1,1,2,3,3,3-heptafluoropropane) and at least one alkylene oxide.

The invention also relates to a sterilizing gas mixture devoid of CFC-115 comprising HFC-125, at least HFC-227ea and at least one alkylene oxide.

Ethylene oxide is preferred as alkylene oxide.

Within the meaning of the present invention, the term "devoid of CFC-115" is understood to denote a CFC-115 content of less than or equal to 10 mg/kg, indeed even of less than or equal to 5 mg/kg. The term "totally devoid of CFC-115" is understood to denote a CFC-115 content below the GC detection limit.

The following examples are intended to illustrate the process according to the invention without, however, limiting it.

EXAMPLES 1 TO 4

200 g of nitrogenous base hydrofluoride shown in the table below and approximately 2 g of limonene were introduced into a 500 ml autoclave made of Inox 316 stainless steel equipped with a stirrer. The system was heated to the reaction temperature and the amount of pure tetrafluoroethylene shown was introduced so as to reach the initial pressure of the reaction. Samples of liquid and gas phase were withdrawn in order to determine the HFC-125 yield by GC (gas chromatography) analysis.

| Example | Organic nitrogenous base hydrofluoride | T (° C.) | TFEe (g) | Initial pressure (bar) | Productive output of HFC-125 (moles per hour and per liter of organic nitrogenous base hydrofluoride) |
|---|---|---|---|---|---|
| 1 | [(C$_2$H$_5$)$_3$N.2,0HF] | 120 | 9 | 10.9 | 0.76 |
| 2 | [(C$_2$H$_5$)$_3$N.2,0HF] | 140 | 8.5 | 12.8 | 1.70 |
| 3 | [(C$_2$H$_5$)$_3$N.2,5HF] | 120 | 9.4 | 10 | 0.47 |
| 4 | [(n-C$_4$N$_9$)$_3$N.2,0HF] | 120 | 8.7 | 10 | 0.18 |

TFEe: tetrafluoroethylene employed

The HFC-125 obtained did not contain CFC-115. No decomposition of the nitrogenous base hydrofluoride was observed.

EXAMPLE 5

200 ml of [(n-C$_4$H$_9$)$_3$N.2.5HF] complex were introduced into a 500 ml autoclave. The system was heated to 120° C. and tetrafluoroethylene (37% by volume, diluted in helium) was introduced continuously. The feed flow rate was 92 mmol of tetrafluoroethylene/hour. The pressure was 20 bar. The residence time was 2 h. The gas phase exiting from the reactor was analysed by GC (gas chromatography). The productive output of HFC-125 was 0.17 mol per hour and per litre of complex.

The test was continued for 550 h without signs of deactivation while regularly adding HF in order to maintain an average HF/(n-C$_4$H$_9$)$_3$N molar ratio of 2.4.

No by-product was detected during the test. The product obtained was devoid of CFC-115.

The invention claimed is:

1. Process for the manufacture of pentafluoroethane, according to which tetrafluoroethylene is subjected to reaction with an organic nitrogenous base hydrofluoride at a temperature of greater than 100° C. and not exceeding 160° C.

2. Process according to claim 1, in which the temperature is from 110 to 150° C.

3. Process according to claim 2, in which the temperature is from 120 to 140° C.

4. Process according to claim 1, in which the pressure is maintained from 2 to 30 bar.

5. Process according to claim 1, in which the organic nitrogenous base hydrofluoride corresponds to the general formula [B*nHF] in which B denotes the organic nitrogenous base and n denotes a whole or decimal number of less than or equal to 4.

6. Process according to claim 5, in which n denotes a number of less than or equal to 3.

7. Process according to claim 5, in which n denotes a number of greater than or equal to 2.

8. Process according to claim 1, in which the organic nitrogenous base is selected from the group consisting of from triethylamine and tri(n-butyl)amine.

9. Process according to claim 8, in which the organic nitrogenous base is triethylamine.

10. Process according to claim 1, in which the reaction is carried out continuously.

11. Process according to claim 3, in which the pressure is maintained from 2 to 30 bar.

12. Process according to claim 11, in which the organic nitrogenous base hydrofluoride corresponds to the general formula [B*nHF] in which B denotes the organic nitrogenous base and n denotes a whole or decimal number of less than or equal to 4.

13. Process according to claim 12, in which n denotes a number of less than or equal to 3.

14. Process according to claim 13, in which n denotes a number of greater than or equal to 2.

15. Process according to claim 14, in which the organic nitrogenous base is triethylamine or tri(n-butyl)amine.

16. Process according to claim 15, in which the organic nitrogenous base is triethylamine.

17. Process according to claim 16, in which the reaction is carried out continuously.

18. Process according to claim 2, in which the temperature is from 130 to 140° C.

19. Process according to claim 17, in which the temperature is from 130 to 140° C.

* * * * *